United States Patent [19]

Knöfel et al.

[11] Patent Number: 4,924,028

[45] Date of Patent: May 8, 1990

[54] PROCESS FOR THE PRODUCTION OF POLYNUCLEAR AROMATIC POLYAMINES

[75] Inventors: Hartmut Knöfel, Odenthal; Michael Brockelt, Leverkusen; Marcel Petinaux; Rudolf Uchdorf, both of Krefeld, all of Fed. Rep. of Germany

[73] Assignee: Bayer Aktiengesellschaft, Leverkusen, Fed. Rep. of Germany

[21] Appl. No.: 335,062

[22] Filed: Apr. 6, 1989

[30] Foreign Application Priority Data

Apr. 12, 1988 [DE] Fed. Rep. of Germany ....... 3812083

[51] Int. Cl.$^5$ .............................................. C07C 87/50
[52] U.S. Cl. .................................... 564/331; 564/333; 564/334
[58] Field of Search ...................... 564/331, 332, 334

[56] References Cited

U.S. PATENT DOCUMENTS

| 3,952,042 | 4/1976 | Knöfel | 260/453 |
| 3,996,283 | 12/1976 | Knoefel | 260/570 |
| 4,061,678 | 12/1977 | Knöfel et al. | 260/570 |
| 4,087,459 | 5/1978 | Knöfel et al. | 260/570 |
| 4,093,658 | 6/1978 | Knöfel et al. | 260/570 |

FOREIGN PATENT DOCUMENTS 2343658 3/1975 Fed. Rep. of Germany .

Primary Examiner—Robert V. Hines
Attorney, Agent, or Firm—Joseph C. Gil; Richard E. L. Henderson

[57] ABSTRACT

This invention relates to an improved process for the preparation of polynuclear aromatic polyamines in which the reaction product is prepared by condensing aniline with formaldehyde in the presence of water and acidic catalysts and is worked up by extraction with a hydrophobic solvent. The acid catalyst that accumulates in the aqueous phase during the extraction process is reused.

5 Claims, No Drawings

PROCESS FOR THE PRODUCTION OF POLYNUCLEAR AROMATIC POLYAMINES

BACKGROUND OF THE INVENTION

This invention relates to an improved process for the preparation of polynuclear aromatic polyamines in which the reaction product is prepared by condensing aniline with formaldehyde in the presence of water and acidic catalysts and is worked up by extraction with a hydrophobic solvent. The acid catalyst that accumulates in the aqueous phase during the extraction process is reused.

It is already known that in the preparation of polynuclear aromatic polyamines by condensation of aniline with formaldehyde in the presence of water and acidic catalysts, the accumulating aqueous reaction mixture can be worked up by extraction with a hydrophobic solvent and that the acid catalyst that accumulates during extraction in the aqueous phase can be reused. See, for example, U.S. Pat. Nos. 4,093,658, 4,087,459, 4,061,678, 3,996,283, and 3,952,042 and DE-OS No. 2,343,658.

The main advantage of the processes according to the above references is the absence of the need to neutralize the catalyst. The catalyst need not be neutralized because it accumulates in the aqueous phase during workup of the acidic reaction mixture by extraction and may be returned to the beginning of the process and reused. In addition, certain variations of this known principle, such as those described in U.S. Pat. Nos. 4,093,658 or 4,087,459, provide for the specific preparation of polyamine mixtures with either an increased or reduced content of 2,4'-isomers. The products obtained by the processes disclosed in the above references correspond in suitability as starting products for the preparation of polyisocyanates to the conventional polyamines of the diphenylmethane series produced by neutralizing the acid catalyst. Thus, the property level of polyurethane foams produced from such polyisocyanate mixtures of the diphenylmethane series is substantially the same in both cases. However, a disadvantage of the processes according to the references cited above is that considerable quantities of hydrophobic solvent and aniline must be used solely for the extraction used for the workup of the end products. As a consequence, these processes involve a considerable amount of distillation in the workup of the organic phase and hence a considerable consumption of energy.

The object of the present invention is to provide a new, improved process for the preparation of polynuclear aromatic polyamines from aniline and formaldehyde in the presence of acidic catalysts. The improved process is intended to improve upon the advantages of the known processes and, in addition, to provide for the preparation of products of improved quality with less distillation and, hence, lower energy consumption. This object is achieved by the process according to the invention which is described in detail hereinafter.

SUMMARY OF THE INVENTION

The present invention relates to a process for the preparation of polynuclear aromatic polyamines by reacting aniline with formaldehyde in the presence of water and acid catalysts in a single-stage or two-stage reaction within a temperature range of from 0° to 180° C. The reaction is optionally preceded by an aminal preliminary step in which N,N'-disubstituted aminal is formed in the absence of acid catalyst and is then converted into the desired end product in one or more stages in the presence of acid catalyst at a temperature in the range from 0° to 180° C. The resultant reaction mixture is then worked up by extraction with a hydrophobic solvent containing aniline. The resultant organic phase is separated and distilled into (i) a distillate consisting of aniline-containing solvent that is reused in the extraction stage, optionally after addition of fresh aniline, and (ii) a distillation residue consisting essentially of end product of the process. The aqueous phase, for which the water comprises water formed during the condensation reaction and water introduced into the system with the aqueous solution of formaldehyde, contains acid catalyst that accumulates during the extraction. The aqueous phase is recycled, with water being removed in a water separator downstream from the aminal preliminary stage and upstream of the first stage of the reaction and/or in an evaporator downstream from the extraction stage and upstream of the first stage of the reaction and the acid catalyst being reused in the reaction. The process is further characterized in that (a) formaldehyde in the form of an aqueous solution is reacted by mixing said formaldehyde in an aminal preliminary stage with an aniline-containing hydrophobic solvent and/or in the first stage of the reaction with an aniline-containing hydrophobic solvent and the recycled aqueous phase containing the catalyst in the form of amine salts, (b) upon completion of the reaction, the resultant two-phase reaction mixture is separated into an aqueous phase and an organic phase in a phase separator upstream of the product extraction stage, (c) organic phase that accumulates in the phase separator is extracted in a re-extraction stage downstream from the product extraction stage using the substantially product-free aqueous phase obtained from the product extraction stage, (d) an aqueous phase that accumulates in the re-extraction stage and which is somewhat product-enriched (due to the introduction of the organic phase from the phase separator) is returned to the reaction process, (e) a product-depleted organic phase that accumulates in the re-extraction stage is used as part of the extractant in the main product extraction stage, (f) the aqueous phase that accumulates in the phase separator is extracted in the product extraction stage with hydrophobic solvent containing aniline and, optionally, end product, (g) the organic phase that accumulates in the product extraction stage is separated in a distillation stage into a distillate consisting of aniline-containing solvent and a distillation residue consisting essentially of end product, and (h) the distillate that accumulates in the distillation stage is separated, optionally after addition of fresh aniline, into two component streams, one component stream being used at the beginning of the process according to (a) above, and the other component stream being used together with the organic phase leaving the re-extraction stage as extractant for the aqueous phase in the product extraction stage.

DESCRIPTION OF THE INVENTION

Figure 1:
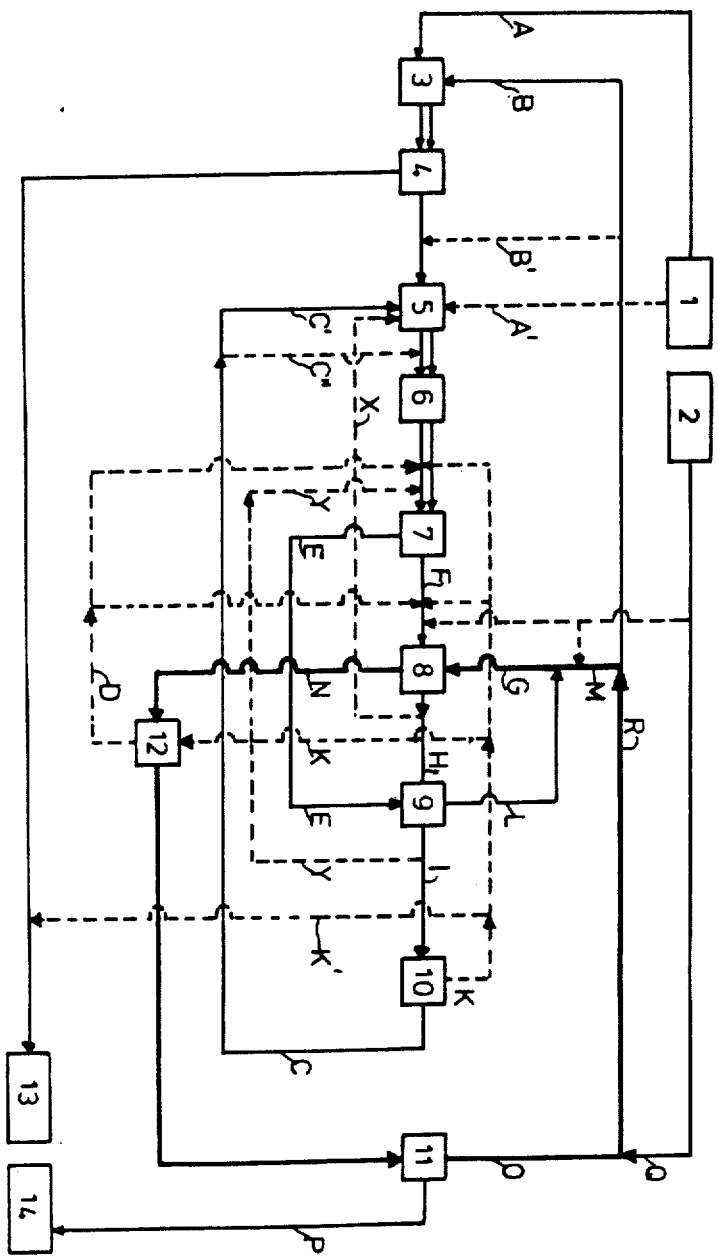
FIGS. 1 and 2 schematically set forth various embodiments of the present invention.

The process according to the invention provides the following advantages relative to the previously known processes:

As in the known processes, the acid catalyst is reused and is not destroyed by neutralization.

The mixtures accumulating as distillate during the distillative workup of the organic phase containing the end products of the process according to the invention may be reused without further separation into their constituents by distillation. These distillates can be used both as extractant for the aqueous phase in the product extraction step and at the beginning of the process, optionally after addition of more aniline.

The process according to the invention can be varied within wide limits with respect to the distribution of homologs in the end products (i.e., ratio of diamines to higher polyamines), although products having a comparatively low content of ortho isomers are always formed.

The polyisocyanates produced from the end products of the process according to the invention surprisingly give polyurethane foams showing a distinctly fainter intrinsic color than corresponding polyurethane foams based on known polyisocyanate mixtures of the diphenylmethane series.

Compared with the known "extraction processes" mentioned above, the total quantity of solvent can be considerably reduced in the process according to the invention. Thus, the concentration of MDA in the organic phases accumulating can be considerably increased and hence the amount of distillation required for working up the organic phases can be correspondingly reduced.

Starting materials for the process according to the invention are aniline and formaldehyde. The formaldehyde is preferably used in the form of an aqueous solution having a formaldehyde content of 20 to 50% by weight.

The hydrophobic solvents used are inert solvents boiling at temperatures in the range from about 30° to about 250° C., preferably in the range from about 80° to about 200° C. Suitable hydrophobic solvents include, for example, chlorobenzene, dichlorobenzenes, benzene, toluene, xylene, dichloroethane, chloroform, and carbon tetrachloride. Preferred hydrophobic solvents include xylenes (i.e., commercial xylene mixtures), particularly o-xylene.

The acid catalyst is a water-soluble acid having a $pK_a$ below 2.5, preferably below 1.5. Suitable acid catalysts include hydrochloric acid, hydrobromic acid, sulfuric acid, trifluoroacetic acid, methanesulfonic acid, and phosphoric acid. Hydrochloric acid is a preferred catalyst. The acids may also be used in admixture with acidic or neutral salts of such acids, such as the corresponding ammonium salts or the corresponding alkali salts, but the use of such salts is less preferred. The acids are present in the circulation system according to the invention in the form of the corresponding ammonium salts of the bases present in the aqueous circuit.

The process according to the invention may be carried out in a single stage or in two stages and with or without a preliminary aminal stage. However, when the reaction is carried out in a single stage, it is always best preceded by an aminal preliminary stage.

As used herein, the term "single-stage reaction" is understood to refer to a variant of the process in which, after addition of the acid catalyst, the aminal is heated within a short period of less than 10 minutes (preferably less than 5 minutes) to an elevated temperature of 60° to 180° C. (preferably 80° to 150° C.) where it is rearranged into the end product, or a variant in which the aminal is directly mixed with the circulated aqueous catalyst phase at the elevated temperature of 60° to 180° C. (preferably 80° to 150° C.) and the mixture subsequently heated if necessary to the desired final temperature.

As used herein, the term "two-stage reaction" is understood to refer to a variant of the process in which, after addition of the acid catalyst or the reaction mixture of aniline, formaldehyde, and acid catalyst, the aminal is first held at 0° to 60° C. (preferably at 30° to 60° C.) for 10 to 90 minutes (preferably for 15 to 60 minutes) in a first stage of the reaction and is then held at 60° to 180° C. (preferably at 60° to 150° C. and more preferably at 100° to 150° C.) for 30 to 180 minutes (preferably for 30 to 120 minutes) in a second stage of the reaction. In this preferred two-stage variant of a multiple-stage reaction, the first stage comprises a rearrangement of the aminal or, in the absence of an aminal preliminary stage, condensation of the starting materials to N-benzylaniline which is rearranged at elevated temperature in the second stage to the nuclear-substituted end product. In one particular variant of the two-stage embodiment (without or, preferably, with an aminal preliminary stage), the first stage is carried out with only a partial stream of the aqueous catalyst phase, generally as less than 50% and preferably less than 15% of the stream. After completion of the first stage and before completion of the last (which is generally the second) stage of the reaction, the reaction is completed in the presence of the entire catalyst phase.

The process may be carried out both continuously and batchwise. When the process is carried out continuously, the times described herein relate to the average residence time of the reaction mixture in the individual stages. When the reaction is preceded by an aminal preliminary stage, the (average) residence time of the starting materials in that stage is generally 10 to 60 minutes and is preferably 15 to 60 minutes.

The temperature in the aminal preliminary stage is generally in the range from about 20° to about 100° C. and is preferably in the range from about 20° to about 60° C. All stages of the process are preferably carried out under the intrinsic pressure of the system and preferably in an inert gas atmosphere (e.g., nitrogen).

Figure 2:
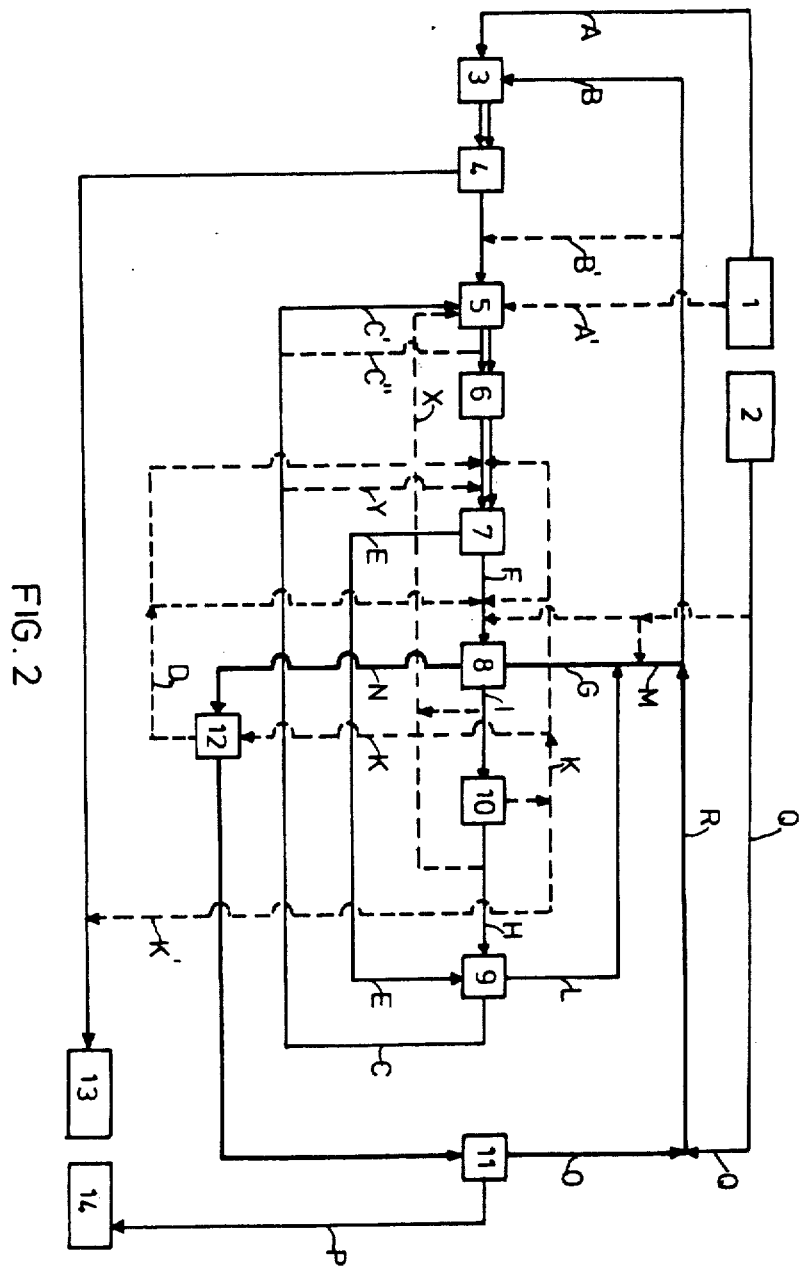

The flow diagrams shown in FIGS. 1 and 2 are intended to illustrate the process according to the invention. In these Figures, the reference numerals have the following meanings:

(1) a tank for aqueous formaldehyde solution,
(2) a tank for aniline,
(3) a condensation reactor (aminal preliminary stage),
(4) a water separator,
(5) the first reaction stage,
(6) the second reaction stage,
(7) a phase separator,
(8) the product extraction stage,
(9) the re-extraction stage,
(10) a water evaporator,
(11) the product distillation stage,

(12) a washing stage,
(13) a tank for wastewater, and
(14) a tank for end product of the process.

The references letters A through R and X and Y denote the product streams referred to below and in the Examples.

In the single stage reaction process, the reaction stages (5) and (6) are combined into a single reaction stage. Both the first and the second reaction stage may be carried out in a single reactor and in several reactors arranged in series. Cascades of stirred tank reactors and/or column reactors arranged in series have proved to be particularly effective for maintaining the residence times indicated. The extraction stage may also be carried out in one or more extractors arranged in series. The usual countercurrent extractors are preferably used for this purpose.

In the simplest case, the distillation stage (11) consists of a distillation column designed in such a way that hydrophobic solvent and aniline can be substantially separated from the end product.

A particular advantage of the process according to the invention is the absence of the need to separate the hydrophobic solvent and aniline. Separation is not needed because the aniline content of the distillate is always less than the amount required for reuse and must be adjusted for reuse by addition of fresh aniline. Thus, it is possible to use energy-saving multistage distillation techniques.

The water formed during the condensation and the water introduced into the system with the aqueous formaldehyde solution must be removed from the system at some suitable point in order to maintain a constant water volume. If a preliminary aminal stage (3) is employed, the water is preferably removed in the water separator (4) before the aminal and the acid catalyst are brought together. If no aminal preliminary stage is employed, the water is preferably removed in a water evaporator (10) placed downstream from the re-extraction stage (9) or placed between the product extraction stage (8) and the re-extraction stage (9). This water evaporator is preferably operated on the principle of flash evaporation by application of vacuum. However, water may in principle also be removed from the system by distillation at any other point.

In the practical application of the process according to the invention, several embodiments or variants are possible and are described in detail below.

In a first preferred embodiment of the process according to the invention (illustrated, for example, in FIG. 1), the aqueous formaldehyde solution (A) is fed into aminal preliminary stage (3), where reaction with a mixture (B) of aniline and hydrophobic solvent takes place. Product stream (B) is part of the distillate (O) from the distillation stage (11), to which is generally added an additional quantity of aniline (Q). The molar ratio of aniline to formaldehyde in the aminal stage is generally between 1.5:1 and 25:1, preferably between 1.8:1 and 10:1. The ratio by weight of aniline to hydrophobic solvent in (B) is generally between 1:4 and 3:1, preferably between 1:1 and 2:1. The reaction in the aminal stage (3) takes place at temperatures within the ranges mentioned above.

Following stage (3), the aqueous phase formed from the water of condensation and the formalin water, and which also contains the water-soluble impurities of the formaldehyde and aniline, is mechanically separated in a separator (4), preferably at a temperature below 60° C.

The residual organic phase of this separation is transferred to the reactor (5) and combined with the aqueous stream (C') at temperatures below 60° C. In this first preferred embodiment of the process according to the invention, stream (C') comprises the entire quantity of catalyst phase (C) to be recycled. The content of aniline-formaldehyde condensates in this phase (C) is generally between 10 and 40% by weight and is preferably between 15 and 30% by weight. Thus, at this point, the total arylamine content (including aniline) is generally from 30 to 70% by weight, preferably from 40 to 60% by weight. The degree of protonation is 25 to 75%, preferably 45 to 65%. As used herein, the term "degree of protonation" refers to the percentage of basic amine nitrogen atoms which are present in the form of ammonium groups, i.e., "protonated." The ratio by weight of catalyst phase (C) to the organic phase from (4) is generally between 1:10 and 100:1, preferably between 0.5:1 and 3:1.

In this first, continuous-method embodiment of the process according to the invention, the reactor (5) represents the "first reaction stage" described above and is operated under the above-mentioned conditions of temperature and reaction time. In general, this reactor consists of a multistage cascade of stirred tank reactors or a single-stage or multistage column reactor in which the temperature rises from around 20° C. at the beginning to 60° C. at the end.

The two-phase reaction mixture is transferred from the first reaction stage (5) to the second reaction stage (6), which also consists of a multistage cascade of stirred tank reactors or of a single-stage or multistage column reactor. This second reaction stage is also operated under the above-mentioned conditions of reaction temperature and average residence time. The two-phase reaction mixture preferably passes through a temperature profile beginning at 60° C. and ending at a temperature of from 95° to 160° C. (preferably from 120° to 140° C.) in reaction stage (6). Using this preferred temperature profile, reaction times of up to 60 minutes in reaction stage (6) are generally sufficient.

The two-phase reaction mixture leaving the second reaction stage (6) is then separated in the phase separator (7) (at temperatures preferably in the range from 80° to 100° C.) into an organic phase (E) and an aqueous phase (F).

The aqueous phase (F) is transferred to the product extraction stage (8). In the product extraction stage (8), which preferably comprises several stages and is preferably operated at temperatures of 80° to 110° C., the end products are extracted from aqueous phase (F) in exchange for aniline and transferred into an organic phase (N). The extractant (G) used in the product extraction stage (8) is a mixture of hydrophobic solvent and aniline and may optionally contain small amounts of aniline-formaldehyde condensates. The ratio by weight of aniline (plus any aniline-formaldehyde condensates) to solvent is generally between 0.5:1 and 3:1, preferably between 1:1 and 2:1. The weight ratio of extractant (G) to aqueous phase (F) is generally between 0.5:1 and 3:1, preferably between 0.7:1 and 2:1.

The organic phase (N) is transferred to the distillation stage (11), optionally after passing through a catalyst washing stage (12) in which any traces of catalyst present are removed. In distillation stage (11), a distillation residue (P), which represents the end product of the process and which is collected in tank (14), is separated by distillation. The distillation stage (11) may consist, for example, of a single stage evaporator which produces a distillate (O) in addition to a distillation residue (P). Besides aniline, the distillate (O) contains all of the hydrophobic solvent from (N) and is used for preparing solutions (B) and (G). However, since the aniline content in distillate (O) is always less than the necessary aniline concentration in the extractant (G), the deficit must be made up, for example, by combining (O) with fresh aniline (Q) from tanks (2), thereby forming product stream (R). Product stream (R) is divided into product streams (B) and (M).

Product stream (B) is returned to the aminal stage (3), whereas product stream (M) is combined with product stream (L) from the re-extraction stage (9) to form the extractant (G). Product stream (B) may also be used with the same composition as distillation (O) at the beginning of the process, so that component stream (M) entering (G) is brought to the desired composition with only a partial quantity of (Q), with the remainder of (Q) being added to and mixed at a suitable point (for example, between stages (6) and (8)) with the two-phase system (i.e., between stages (6) and (7)) or with the aqueous phase (i.e., between stages (7) and (8)).

The aqueous phase (H) from the main extraction stage (8), which contains only very small amounts (less than 5% by weight and preferably less than 2% by weight) of process products (aniline-formaldehyde condensates), is extracted in the multistage re-extraction stage (9), generally at temperatures of 40° to 110° C. The extractant in this re-extraction stage (9) is product stream (E), the organic phase separated off in separator (7). The process products contained in (E) are exchanged almost completely for aniline and transferred to an aqueous phase (I), resulting in an organic phase (L) which is substantially free from products of the process.

The organic phase (L) from the re-extraction stage (9) is a component part of the extractant (G). Thus, the extractant is generally formed by combining the partial quantity (M) of stream (R) with organic phase (L). However, the extraction in stage (8) may also be carried out in a multistage extractor by initially using stream (M) alone in the first part or the last part (with reference to the aqueous phase) of the product extraction stage (8) and by feeding stream (L) in a later part or an earlier part (with reference to the aqueous phase) of the product extraction stage (8).

The aqueous phase (I) that accumulates in re-extraction stage (9), may be used as the catalyst solution (C) to be recycled. However, a quantity of water (K), which may generally make up as much as 80% by weight of the water present in (8), but which is preferably less than 50% by weight, is removed from aqueous phase (I) in evaporator (10). This quantity of water (K) is added to the reaction mixture between the second reaction stage (6) and the main extraction stage (8) or is used to wash out final traces of catalyst from the organic phase (N) in the catalyst washing stage (12) for subsequent addition to the reaction mixture as product stream (D) between stages (6) and (8). When this procedure for removal of water in evaporator (10) and recycling is adopted, the reaction in reactors (5) and (6) is carried out using a lower water content in the aqueous phase than is used in the extraction in extraction stage (8). This procedure can thus often facilitate the extraction in stage (8).

The first preferred embodiment of the process according to the invention described above may be modified in various ways.

In a first variant of the first preferred embodiment, aminal stage (3) is completely or partly eliminated. In practice, this means that a partial quantity of the mixture of aniline and hydrophobic solvent (B') and a partial quantity of the aqueous formaldehyde (A') used in the reaction are not introduced into aminal stage (3), but rather upstream of the first reaction stage (5). In the extreme case of a complete absence of an aminal preliminary stage, the total quantity of the mixture of aniline and hydrophobic solvent and the total quantity of aqueous formaldehyde may be delivered directly to the first reaction stage (5). In the absence of an aminal preliminary stage, however, the reaction always must be carried out in two stages using the reaction stages (5) and (6), as described above. Where this procedure is adopted, the introduced water and the water of condensation are, of course, only partly removed by the phase separator (4), if removed at all. Removal of this water would then be possible, for example, by diverting from the distillate from evaporator (10) a partial stream (K') which is directly introduced into the wastewater tank (13).

In a second variant, reaction stages (5) and (6) may be combined into a single reaction stage operated under the above-mentioned conditions of reaction temperature and reaction time. When carried out in a single stage, however, the reaction always must be preceded by an aminal preliminary stage (3).

In both the first variant and the second variant, the product streams are regulated in such a way that a molar ratio of aniline to formaldehyde of 1.5:1 to 25:1 is present in stage (5), with the arylamine introduced with catalyst stream (C) being included in the calculation.

In a third variant combined with the first variant, the recycled catalyst solution (C) is divided into two streams such that the reaction in the first stage takes place in the presence of only part (C') of the recycled catalyst solution, with the remaining quantity of catalyst solution (C") being added between the reaction stages (5) and (6). The weight ratio between the organic phase in stage (5) and aqueous phase (C') (initially introduced, for example, in the first stirred tank reactor of stage (5)) is between 1:1 and 100:1, preferably between 3:1 and 30:1.

In a fourth variant combined with the variants mentioned above, a partial quantity (X) of up to 50% by weight (preferably up to 15% by weight) of the entire aqueous phase from product extraction stage (8) is removed from the aqueous phase leaving stage (8) and returned to the first stage of the reaction. The entire quantity of recycled catalyst phase (C) is preferably introduced into the system as stream (C"') downstream from stage (5). The catalyst in stage (5) then consists almost exclusively of aniline hydrochlorides present in (X), while the catalyst phase (C) contains, in addition to aniline hydrochlorides, hydrochlorides of process products.

In a fifth variant, which may be combined with the preceding variants, a partial stream (Y) is removed from aqueous phase (I) leaving the re-extraction stage (9) and returned to the reaction mixture upstream of separator (7). This variant is particularly useful in reducing the ratio of organic phase to aqueous phase in re-extraction stage (9), thereby enabling the re-extraction stage (9) to be operated under optimal conditions, i.e., at weight ratio of organic phase (E) to aqueous phase (H) of less than 1.5:1, preferably of less than 1:1.

A second embodiment of the process according to the invention (illustrated, for example, in FIG. 2) is distinguished from the first preferred embodiment by the arrangement of the evaporator stage (10) upstream of the re-extraction stage (9). This second embodiment is also amenable to the variants described above for the first embodiment, although stream (X) in the fourth variant may also be removed downstream from the evaporator stage (10) and upstream of the re-extraction stage (9) and stream (Y) in the fifth variant may form part of the recycled aqueous catalyst solution (C).

Reversal of the order of stages (9) and (10), as illustrated in FIG. 2, results in an increase in the ratio of organic phase (E) to aqueous phase (H) for a given quantity of acid in phase (H), thereby allowing the efficiency of the re-extraction stage (9) to be optimized.

The main purpose of the re-extraction stage (9) is to remove aniline-formaldehyde condensates almost completely from the organic phase (E), an objective which is generally achieved when the phase ratio by weight of (E) to (H) is below 1.5:1, preferably below 1:1.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight. The term "polyarylamine" is used generically to include all the polyamines of the diphenylmethane series present in mixtures in the respective product streams.

EXAMPLES

EXAMPLE 1 (FIG. 1)

In a reactor (3) consisting of two stirred tanks arranged one after the other, a 30% aqueous formalin solution (product stream (A)) is reacted at 40° C. with an aniline-xylene mixture (product stream (B)).

(A) 0.375 kg/h formaldehyde
  0.875 kg/h water
(B) 2.327 kg/h aniline
  1.940 kg/h o-xylene In a water separator (4), the lower aqueous phase is separated as wastewater and collected in a wastewater tank (13). The upper organic phase is transferred to a second reactor (5) consisting of three stirred tanks in which the organic phase is mixed with the product stream (C).

(C) 0.881 kg/h polyarylamine
  0.563 kg/h aniline
  0.328 kg/h hydrochloric acid
  1.975 kg/h water The temperatures in the three tanks of the reactor (5) are regulated at, in sequence, 30° C., 40° C., and 60° C.

Another reactor (6) likewise consists of three stirred tanks in which the temperatures are regulated by heating at 100° C., 135° C., and 140° C. at the intrinsic pressure of the system.

After the reaction mixture cools to 95° C. and expands to normal pressure, the HCl wash water from the washing stage (12) (product stream (D)) is added. The organic phase (product stream (E)) and the aqueous phase (product stream (F)) are then separated from each other in the phase separator (7).

(E) 0.870 kg/h polyarylamine
  0.703 kg/h aniline
  1.940 kg/h o-xylene
(F) 2.130 kg/h polyarylamine
  0.218 kg/h aniline
  0.328 kg/h hydrochloric acid
  2.881 kg/h water The aqueous phase (F) is then continuously extracted by countercurrent extraction with an aniline-xylene mixture (product stream (G)) in the extraction column (8)

(G) 0.038 kg/h polyarylamine
  4.159 kg/h aniline
  4.143 kg/h o-xylene
changing into the polyarylamine-depleted aqueous phase (H)
(H) 0.049 kg/h polyarylamine
  1.370 kg/h aniline
  0.328 kg/h hydrochloric acid
  2.881 kg/h water
which is used in another extraction column (9) for the countercurrent extraction of the organic phase (E) separated in phase separator (7).

The aqueous phase (product stream (I)) that accumulates in (9), which is enriched with polyarylamine in relation to the aqueous phase (H),
(I) 0.881 kg/h polyarylamine
  0.563 kg/h online
  0.328 kg/h hydrochloric acid
  2.881 kg/h water
is concentrated in the distillation stage (10), with concomitant removal of the distillate as product stream (K), and is then returned to the reactor (5) as product stream (C).

(K) 0.906 kg/h water

The organic phase that accumulates in extraction stage (9), in which the polyarylamine content is depleted relative to (E), is used as the product stream (L) component of extractant in product extraction stage (8). Product stream (L) and the aniline-xylene mixture (M) together constitute product stream (G), which forms the total quantity of extractant used in product extraction stage (8).

(L) 0.038 kg/h polyarylamine
  1.510 kg/h aniline
  1.940 kg/h o-xylene
(M) 2.649 kg/h aniline
  2.203 kg/h o-xylene The organic phase containing the reaction product which accumulates in the product extraction stage (8) (product stream (N)) is extracted in another three- to five-stage extraction column (washing stage (12)), with the distillate from distillation stage (10) consisting essentially of water (product stream (K)).

(N) 2.119 kg/h polyarylamine
  3.007 kg/h aniline
  4.143 kg/h o-xylene
(K) 0.906 kg/h water In the washing stage (12), the HCl content of the product stream (N), which amounts to about 0.2–0.3% by weight, is reduced under the described conditions to less than 0.01% by weight. The HCl-containing wash water is recycled into the reaction mixture between stages (6) and (7) as product stream (D). The organic phase leaving the washing stage is separated in a distillation stage (11) into a distillate (product stream (O)) and a distillation residue (product stream (P)).

(O) 3.007 kg/h aniline
    4.143 kg/h o-xylene
(P) 2.119 kg/h polyarylamine

After addition of fresh aniline (product stream (Q)) from storage tank (2) to product stream (O), the aniline-xylene mixture thus prepared (product stream (R)) is divided and used as product streams (B) and (M).

The distillation residue (product stream (P)) of the distillation stage (11) has the following composition:
0.2% 2,2'-diaminodiphenylmethane
4.3% 2,4'-diaminodiphenylmethane
46.3% 4,4'-diaminodiphenylmethane
0.2% N-methyl-substituted diaminodiphenylmethanes
22.2% triamines
11.1% tetramines
15.6% polyamines of higher than tetrafunctionality

EXAMPLE 2 (FIG. 1)

In a reactor (3) consisting of two stirred tanks arranged one after the other, a 30% aqueous formalin solution (product stream (A)) from storage tank (1) is reacted at 40° C. with an aniline-xylene mixture (product stream (B)).

(A) 0.500 kg/h formaldehyde
    1.166 kg/h water
(B) 3.103 kg/h aniline
    2.586 kg/h o-xylene In a water separator (4), the lower aqueous phase is separated as wastewater and collected in a wastewater tank (13). The upper organic phase is transferred to a second reactor (5) consisting of three stirred tanks in which the organic phase is mixed with the product stream (C).

(C) 0.805 kg/h polyarylamine
    1.771 kg/h aniline
    0.586 kg/h hydrochloric acid
    3.530 kg/h water The temperatures in the three tanks of the reactor (5) are regulated at, in sequence, 35° C., 50° C., and 60° C.

Another reactor (6) likewise consists of three stirred tanks in which the temperatures are regulated by heating at 100° C., 135° C., and 140° C. at the intrinsic pressure of the system.

After the reaction mixture cools to 95° C. and expands to normal pressure, the HCl wash water from the washing stage (12) (product stream (D)) is added. The organic phase (product stream (E)) and the aqueous phase (product stream (F)) are then separated from each other in the phase separator (7).

(E) 0.734 kg/h polyarylamine
    1.460 kg/h aniline
    2.586 kg/h o-xylene
(F) 2.897 kg/h polyarylamine
    0.779 kg/h aniline
    0.586 kg/h hydrochloric acid
    5.148 kg/h water The aqueous phase (F) is then continuously extracted by countercurrent extraction with an aniline-xylene mixture (product stream (G)) in the extraction column (8)

(G) 0.048 kg/h polyarylamine
    7.893 kg/h aniline
    7.215 kg/h o-xylene
changing into the polyarylamine-depleted aqueous phase (H)

(H) 0.110 kg/h polyarylamine
    2.650 kg/h aniline
    0.586 kg/h hydrochloric acid
    5.148 kg/h water
which is used in another extraction column (9) for the countercurrent extraction of the organic phase (E) separated in phase separator (7).

The aqueous phase (product stream (I)) that accumulates in (9), which is enriched with polyarylamine in relation to the aqueous phase (H), (I) 0.805 kg/h polyarylamine
    1.771 kg/h aniline
    0.586 kg/h hydrochloric acid
    5.148 kg/h water
is concentrated in the distillation stage (10), with concomitant removal of the distillate as product stream (K), and is then returned to the reactor (5) as product stream (C).

(K) 1.618 g/h water.

The organic phase that accumulates in extraction stage (9), in which the polyarylamine content is depleted relative to (E), is used as the product stream (L) component of extractant in product extraction stage (8). Product stream (L) and the aniline-xylene mixture (M) together constitute product stream (G), which forms the total quantity of extractant used in product extraction stage (8).

(L) 0.048 kg/h polyarylamine
    2.339 kg/h aniline
    2.586 kg/h o-xylene
(M) 5.554 kg/h aniline
    4.629 kg/h o-xylene The organic phase containing the reaction product which accumulates in the product extraction stage (8) (product stream (N)) is extracted in another three- to five-stage extraction column (washing stage (12)), with the distillate from distillation stage (10) consisting essentially of water (product stream (K)).

(N) 2.835 kg/h polyarylamine
    6.022 kg/h aniline
    7.215 kg/h o-xylene
(K) 1.619 kg/h water In the washing stage (12), the HCl content of the product stream (N), which amounts to about 0.2-0.3% by weight, is reduced under the described conditions to less than 0.01% by weight. The HCl-containing wash water is recycled into the reaction mixture between stages (6) and (7) as product stream (D). The organic phase leaving the washing stage (12) is separated in a distillation stage (11) into a distillate (product stream (O)) and a distillation residue (product stream (P)).

(O) 6.027 kg/h aniline
    7.215 kg/h o-xylene
(P) 2.835 kg/h polyarylamine

After addition of fresh aniline (product stream (Q)) from storage tank (2) to product stream (O), the aniline-xylene mixture thus prepared (product stream (R)) is divided and used as product streams (B) and (M).

The distillation residue (product stream (P)) of the distillation stage (11) has the following composition:
0.4% 2,2'-diaminodiphenylmethane
5.9% 2,4'-diaminodiphenylmethane
58.7% 4,4'-diaminodiphenylmethane
0.2% N-methyl-substituted diaminodiphenylmethanes
20.5% triamines
7.7% tetramines
6.6% polyamines of higher than tetrafunctionality

EXAMPLE 3 (FIG. 1)

In a reactor (3) consisting of two stirred tanks arranged one after the other, a 30% aqueous formalin solution (product stream (A)) is reacted at 40° C. with an aniline-xylene mixture (product stream (B)).

(A) 0.500 kg/h formaldehyde
  1.166 kg/h water
(B) 3.103 kg/h aniline
  2.586 kg/h o-xylene In a water separator (4), the lower aqueous phase is separated as wastewater and collected in a wastewater tank (13). The upper organic phase is transferred to a second reactor (5) consisting of three stirred tanks in which the organic phase is mixed with the product stream (C).

(C) 0.924 kg/h polyarylamine
  1.000 kg/h aniline
  0.437 kg/h hydrochloric acid
  2.634 kg/h water The temperatures in the three tanks of the reactor (5) are regulated at, in sequence, 35° C., 50° C., and 60° C.

Another reactor (6) likewise consists of three stirred tanks in which the temperatures are regulated by heating at 100° C., 135° C., and 140° C. at the intrinsic pressure of the system.

After the reaction mixture cools to 95° C. and expands to normal pressure, the organic phase (product stream (E)) and the aqueous phase (product stream (F)) are then separated from each other in the phase separator (7). The HCl wash water from the washing stage (12) (product stream (D)) is then added to the aqueous phase (F).

(E) 0.910 kg/h polyarylamine
  1.187 kg/h aniline
  2.586 kg/h o-xylene
(F) 2.844 kg/h polyarylamine
  0.286 kg/h aniline
  0.437 kg/h hydrochloric acid
  2.634 kg/h water The aqueous phase (F) is then continuously extracted by countercurrent extraction with an aniline-xylene mixture (product stream (G)) in the extraction column (8)

(G) 0.048 kg/h polyarylamine
  5.592 kg/h aniline
  5.523 kg/h o-xylene changing into the polyarylamine-depleted aqueous phase (H)

(H) 0.062 kg/h polyarylamine
  1.823 kg/h aniline
  0.437 kg/h hydrochloric acid
  3.841 kg/h water which is used in another extraction column (9) for the countercurrent extraction of the organic phase (E) separated in phase separator (7).

The aqueous phase (product stream (1)) that accumulates in (9), which is enriched with polyarylamine in relation to the aqueous phase (H), (I) 0.924 kg/h polyarylamine
  1.000 kg/h aniline
  0.437 kg/h hydrochloric acid
  3.841 kg/h water is concentrated in the distillation stage (10), with concomitant removal of the distillate as product stream (K), and is then returned to the reactor (5) as product stream (C).

(K) 1.207 g/h water

The organic phase that accumulates in extraction stage (9), in which the polyarylamine content is depleted relative to (E), is used as the product stream (L) component of extractant in product extraction stage (8). Product stream (L) and the aniline-xylene mixture (M) together constitute product stream (G), which forms the total quantity of extractant used in product extraction stage (8).

(L) 0.048 kg/h polyarylamine
  2.060 kg/h aniline
  2.586 kg/h o-xylene
(M) 3.532 kg/h aniline
  2.037 kg/h o-xylene The organic phase containing the reaction product which accumulates in the product extraction stage (8) (product stream (N)) is extracted in another three- to five-stage extraction column (washing stage (12)), with the distillate from distillation stage (10) consisting essentially of water (product stream (K)).

(N) 2.830 kg/h polyarylamine
  4.005 kg/h aniline
  5.523 kg/h o-xylene
(K) 1.207 kg/h water In the washing stage (12), the HCl content of the product stream (N), which amounts to about 0.2–0.3% by weight, is reduced under the described conditions to less than 0.01% by weight. The HCl-containing wash water is recycled into the reaction mixture as product stream (D). The organic phase leaving the washing stage (12) is separated in a distillation stage (11) into a distillate (product stream (O)) and a distillation residue (product stream (P)).

(O) 4.005 kg/h aniline
  5.523 kg/h o-xylene
(P) 2.830 kg/h polyarylamine

After addition of fresh aniline (product stream (Q)) from storage tank (2) to product stream (O), the aniline-xylene mixture thus prepared (product stream (R)) is divided and used as product streams (B) and (M).

The distillation residue (product stream (P)) of the distillation stage (11) has the following composition:

0.3% 2,2'-diaminodiphenylmethane
  4.4% 2,4'-diaminodiphenylmethane
  50.5% 4,4'-diaminodiphenylmethane
  0.2% N-methyl-substituted diaminodiphenylmethanes
  20.7% triamines
  10.1% tetramines
  13.8% polyamines of higher than tetrafunctionality Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of polynuclear aromatic polyamines by reacting aniline with formaldehyde in the presence of water and an acid catalyst in a single-stage or two-stage reaction within a temperature range of from 0° to 180° C., optionally preceded by an aminal preliminary step in which an N,N'-disubstituted aminal is formed in the absence of acid catalyst and then converted into the desired polynuclear aromatic polyamine end product in one or more stages in the presence of an acid catalyst at a temperature in the range from 0° to 180° C., thereby forming a reaction mixture; working up the reaction mixture by extraction with a hydrophobic solvent containing aniline, said extraction producing an organic phase and an aqueous phase; separating the organic phase from the aqueous phase; distilling the organic phase into (i) a distillate consisting of aniline-containing solvent, said distillate being reused in the extraction stage, optionally after addition of fresh aniline, and (ii) a distillation residue consisting essentially of the polynuclear aromatic polyamine end product; recycling the aqueous phase containing the acid catalyst, wherein water is removed in a water separator downstream from the aminal preliminary stage and upstream of the first stage of the reaction and/or in an evaporator downstream from the extraction stage and upstream of the first stage of the reaction, and wherein the acid catalyst is reused in the reaction; said process further characterized in that (a) formaldehyde in the form of an aqueous solution is reacted by mixing said formaldehyde in an aminal preliminary stage with an aniline-containing hydrophobic solvent and/or in the first stage of the reaction with an aniline-containing hydrophobic solvent and the recycled aqueous phase containing the catalyst in the form of amine salts;

(b) upon completion of the reaction, the resultant two-phase reaction mixture is separated into an aqueous phase and an organic phase in a phase separator upstream of the product extraction stage;

(c) the organic phase that accumulates in the phase separator is extracted in a re-extraction stage downstream from the product extraction stage using substantially product-free aqueous phase obtained from the product extraction stage;

(d) an aqueous phase that accumulates in the re-extraction stage and which is product-enriched due to the introduction of the organic phase from the phase separator is returned to the reaction;

(e) a product-depleted organic phase that accumulates in the re-extraction stage is used as part of the extractant in the main product extraction stage;

(f) the aqueous phase that accumulates in the phase separator is extracted in the product extraction stage with hydrophobic solvent containing aniline and, optionally, end product, (g) the organic phase accumulating in the product extraction stage is separated in a distillation stage into a distillate consisting of aniline-containing solvent and a distillation residue consisting essentially of end product; and (h) the distillate that accumulates in the distillation stage is separated, optionally after addition of fresh aniline, into two component streams, one component stream being used at the beginning of the process according to (a) above and the other component stream being used together with the organic phase leaving the re-extraction stage as extractant for the aqueous phase in the product extraction stage.

2. A process according to claim 1 wherein a quantity of water equivalent to up to 80% by weight of the water present in the aqueous phase of the extraction stage is removed by distillation from the aqueous phase downstream of the extraction stage before said aqueous phase is reused and said quantity of water is then added to the reaction mixture between the last reaction stage and the product extraction stage.

3. A process according to claim 2 wherein the quantity of water removed by distillation is used to wash out catalyst from the organic phase of the product extraction stage in a catalyst washing stage before said quantity of water is added to the reaction mixture between the last reaction stage and the product extraction stage.

4. A process according to claim 1 wherein the aqueous phase containing the catalyst to be reused is divided into two component streams, one component stream being introduced into the first reaction stage and the other component stream being added to the reaction mixture downstream from the first reaction stage and upstream of the last reaction stage.

5. A process according to claim 2 wherein the aqueous phase containing the catalyst to be reused is divided into two component streams, one component stream being introduced into the first reaction stage and the other component stream being added to the reaction mixture downstream from the first reaction stage and upstream of the last reaction stage.

* * * * *

UNITED STATES PATENT AND TRADEMARK OFFICE
CERTIFICATE OF CORRECTION

PATENT NO. : 4,924,028

DATED : May 8, 1990

INVENTOR(S) : Knofel et al

Page 1 of 3

It is certified that error appears in the above-identified patent and that said Letters Patent is hereby corrected as shown below:

On the title page, following the Abstract and immediately after "5 Claims:, change "No Drawings" to --2 Drawing Sheets--.

The sheets of drawings, consisting of Figs. 1 and 2, should be added as shown on the attached pages.

At column 10, line 31, please change "online" to --aniline--.

Signed and Sealed this

Twenty-fourth Day of November, 1992

Attest:

DOUGLAS B. COMER

Attesting Officer

Acting Commissioner of Patents and Trademarks